(12) United States Patent
Halili

(10) Patent No.: US 7,497,850 B2
(45) Date of Patent: Mar. 3, 2009

(54) MEDICAL DEVICE NEEDLE RECEIVING PORT

(75) Inventor: Edgardo C. Halili, Santa Clarita, CA (US)

(73) Assignee: Infusion Systems, LLC, Sylmar, CA (US)

( * ) Notice: Subject to any disclaimer, the term of this patent is extended or adjusted under 35 U.S.C. 154(b) by 540 days.

(21) Appl. No.: 11/069,296

(22) Filed: Feb. 28, 2005

(65) Prior Publication Data

US 2005/0197636 A1    Sep. 8, 2005

Related U.S. Application Data

(60) Provisional application No. 60/549,288, filed on Mar. 2, 2004.

(51) Int. Cl.
*A61M 31/00* (2006.01)

(52) U.S. Cl. ................................. 604/288.01

(58) Field of Classification Search ..............
604/288.01–288.04, 30, 891.1, 93.01, 228.02, 604/167.02, 167.03
See application file for complete search history.

(56) References Cited

U.S. PATENT DOCUMENTS

| 3,951,147 | A |   | 4/1976  | Tucker et al.    |            |
|-----------|---|---|---------|------------------|------------|
| 5,108,377 | A |   | 4/1992  | Cone et al.      |            |
| 5,180,365 | A |   | 1/1993  | Ensminger et al. |            |
| 5,476,451 | A | * | 12/1995 | Ensminger et al. | 604/288.03 |
| 5,520,643 | A |   | 5/1996  | Ensminger et al. |            |
| 5,695,490 | A |   | 12/1997 | Flaherty et al.  |            |
| 5,702,363 | A | * | 12/1997 | Flaherty         | 604/288.01 |
| 5,840,063 | A |   | 11/1998 | Flaherty         |            |
| 6,013,051 | A |   | 1/2000  | Nelson           |            |
| 6,293,922 | B1|   | 9/2001  | Haase            |            |
| 2002/0032416 | A1| * | 3/2002 | Utterberg et al. | 604/288.04 |
| 2003/0213459 | A1|   | 11/2003 | Hofmann et al.  |            |

FOREIGN PATENT DOCUMENTS

WO  WO-2005/084274 A3  11/2006

* cited by examiner

*Primary Examiner*—Matthew F DeSanto
(74) *Attorney, Agent, or Firm*—Henricks, Slavin & Holmes LLP

(57) ABSTRACT

A medical device needle receiving port configured to stop a needle's penetration without physically engaging the needle's tip thereby reducing the likelihood of tip damage. The port preferably incorporates a particulate chamber for collecting particulates larger then a fluid outlet dimension.

11 Claims, 6 Drawing Sheets

MEDICAL DEVICE NEEDLE RECEIVING PORT

RELATED APPLICATION

This application claims the benefit of U.S. provisional application 60/549,288 filed 2 Mar. 2004.

FIELD OF THE INVENTION

This invention relates generally to medical devices and more particularly to a port suitable for use in an implantable drug delivery device for exchanging fluid with a hypodermic needle.

BACKGROUND OF THE INVENTION

Various medical devices, e.g., implantable drug delivery devices, have one or more needle receiving ports (e.g. to access a reservoir or a catheter) which may include a needle access hole dimensioned to deny access to needles larger than a predetermined diameter. For example, U.S. Pat. No. 6,293,922 describes a port comprised of a conical depression leading to a central access hole which has "a diameter substantially the same as the predetermined diameter for preventing access to the septum" by oversized hypodermic needles. Needles having diameters smaller than the predetermined diameter are able to pass through the access hole and septum to exchange fluid with the reservoir or catheter. Generally, a physical stop, e.g., a pad made of firm, biocompatible polymer material, is inserted below the septum to engage the needle's tip to limit penetration and provide a tactile feedback to the user advising that the tip of the needle has bottomed. Unfortunately, however, the fragile needle tip can sometimes engage a surface which may cause it to curl up like a fish hook. The hook portion can then damage the septum when the needle is withdrawn from the port.

Implantable medical device ports may also incorporate some type of filtering means, e.g., a sintered or mesh material, to prevent the introduction of particulate matter into the reservoir or catheter.

SUMMARY OF THE INVENTION

The present invention is directed to a medical device needle receiving port configured to stop a needle's penetration without physically engaging the needle's tip thereby reducing the likelihood of tip damage.

Typical hypodermic needles have a cannula or barrel portion whose outer diameter D1 indicates the needle's size, e.g., a 25 gauge needle has an outer diameter between 0.0205 and 0.0195 inches. The distal end of the cannula typically includes a beveled surface which forms a needle point end having an axial length L1 and an outer diameter which diminishes from D1 adjacent to the cannula to D2 at the needle tip. A port, in accordance with the present invention, includes a needle stop member having a hole defining a diameter D3 where D1>D3>D2 such that the needle point end can extend into the hole but is prevented from passing therethrough as a consequence of the point end surface engaging the stop member adjacent to the hole. The hole is configured to define an obstruction-free axial length, or depth, L2 where L2>L1. Thus, the fragile needle tip is prevented from engaging any stop surface and damage to the tip is avoided.

A port in accordance with the invention preferably also includes a particulate collection chamber located beyond the needle stop hole. The collection chamber has one or more fluid outlets dimensioned to prevent particulate matter, introduced by the needle's insertion, from passing through to the reservoir or catheter.

DETAILED DESCRIPTION

Figure 1:
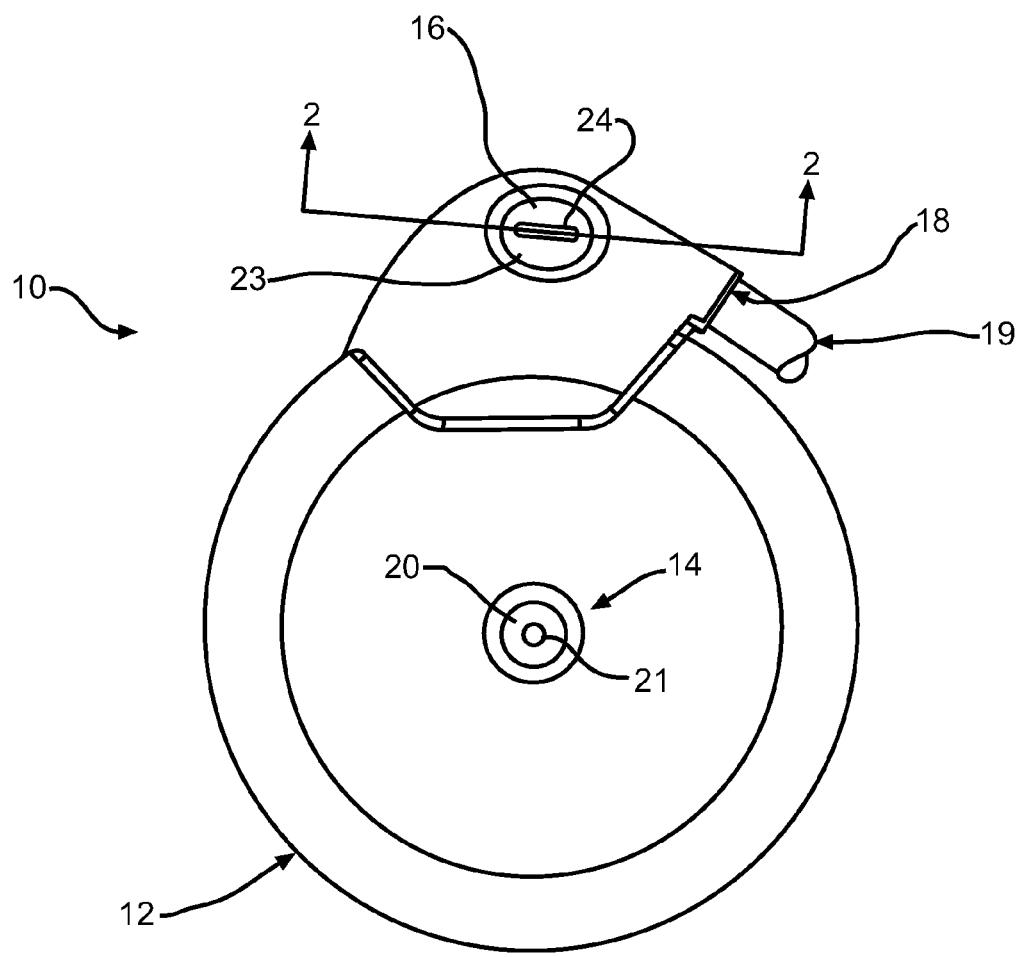
FIG. 1 is a plan view of an exemplary implantable drug delivery device having two needle receiving ports.
Figure 2:
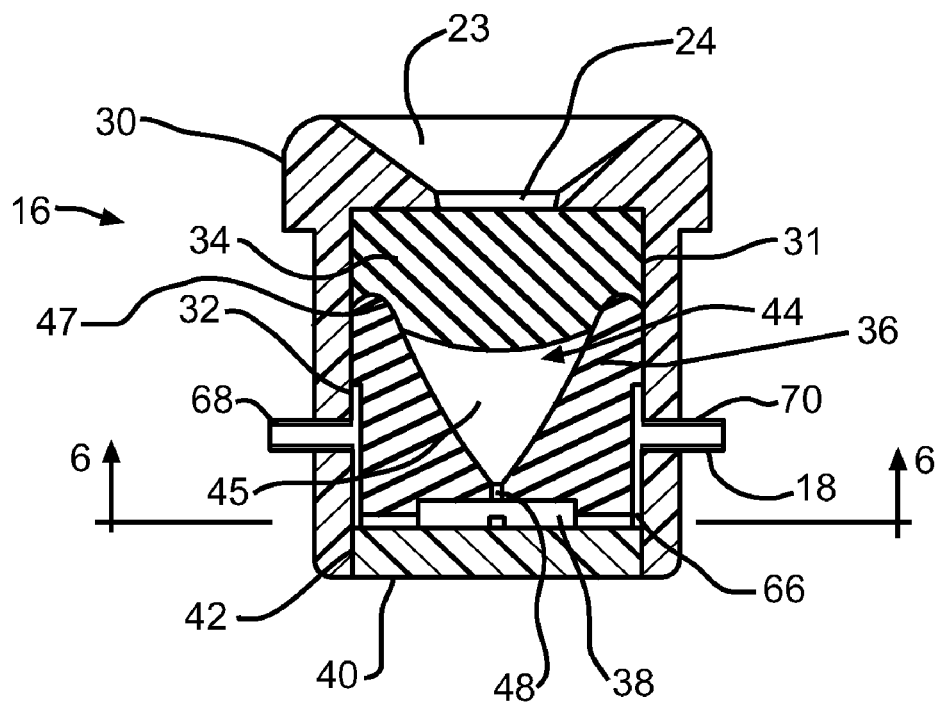
FIG. 2 is an enlarged sectional view taken substantially along the plane 2-2 of FIG. 1 showing a preferred port construction in accordance with the present invention.
Figure 3:
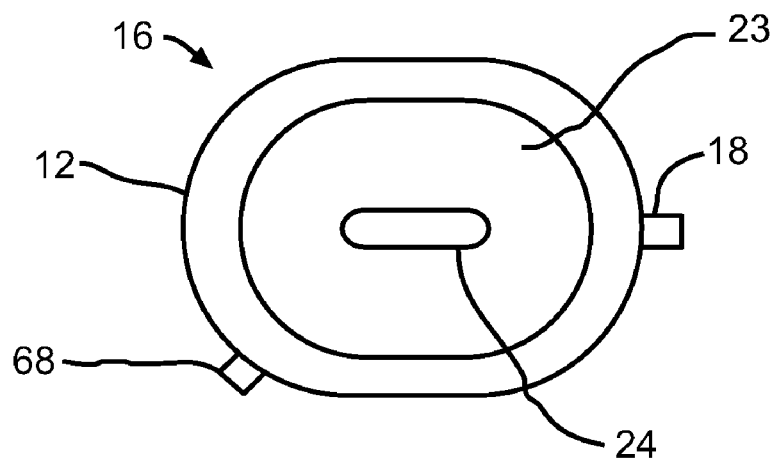
FIG. 3 is a plan view of FIG. 2 showing the port entrance opening.

Attention is initially directed to FIG. 1 which is a plan view of an exemplary implantable drug delivery device 10 intended to be configured in accordance with the present invention. The device 10 comprises a housing 12 enclosing an interior volume (not shown) and defining first and second needle receiving ports 14 and 16. Port 14 is adapted for accessing an internal fluid drug reservoir (not shown) to fill or evacuate the reservoir. Port 16 is adapted for accessing, via port 18, a catheter 19 to either extract a sample and/or introduce a fluid into the catheter. The housing 12 includes one or more interior fluid passageways (not shown) for coupling the reservoir via a controllable fluid transfer device (not shown), e.g., a pump or valve, to the port 16 for delivering fluid medication via catheter 19 to a patient's body site.

As depicted in FIG. 1, port 14 typically includes a conical side wall 20 converging toward a central needle receiving entrance hole 21. The hole 21 is preferably dimensioned to have a diameter small enough to prevent the entry of needles larger than a given size. As depicted, port 16 includes a side wall 23 converging toward a needle receiving entrance opening 24 which is shown for exemplary purposes as comprising a slot having a width narrow enough to prevent the entry of needles larger than a given size. A port in accordance with the present invention (FIGS. 2-6) can be configured with an entrance opening in the form of either a hole, e.g. 21, or a slot, e.g. 24.

Attention is now directed to FIGS. 2-6 which illustrate a preferred embodiment of an exemplary port, e.g., port 16, in accordance with the present invention. The needle receiving port 16 is comprised of an inverted cup shaped port body 30 defining an interior cavity 31 having an internal diameter 32. A septum 34, typically a pliable self healing membrane, is mounted in the cavity 31 above a needle stop member 36. A bottom cover 40 is sealed along interface 42 to the inside wall of cavity 31 to retain the septum 34 and stop member 36 in place. The sealed interface 42 is fluid tight to prevent leakage.

The needle stop member 36, in a preferred embodiment, includes a funnel shaped recess 44 having a side wall 45 which converges from an entrance mouth 47 to a needle stop hole 48. In accordance with the present invention, the hole 48 has a diameter D3 (FIG. 4A) selected such that D3 is less than the outer diameter D1 of the cannula of an acceptable hypodermic needle N1 (FIG. 4A).

Figure 4A:
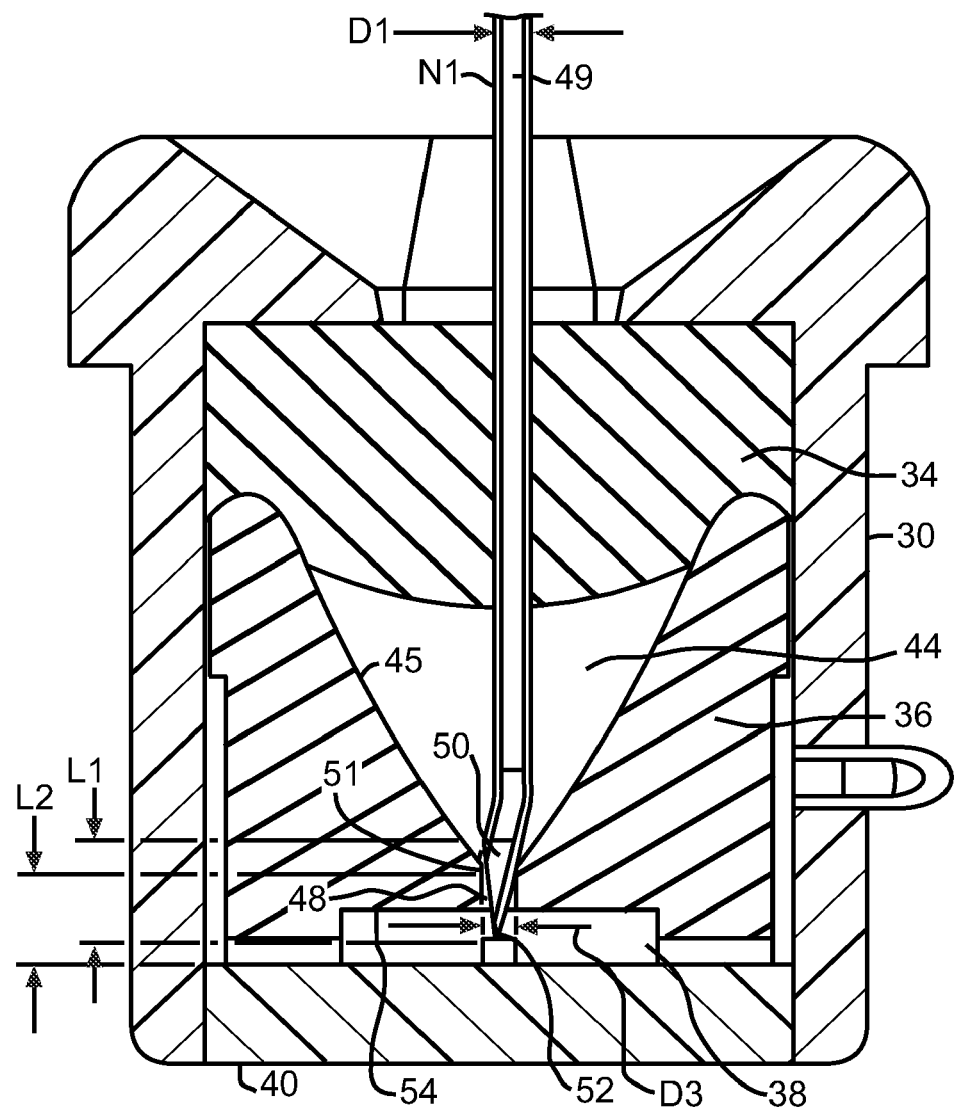
FIG. 4A is an enlarged view of FIG. 2 showing how the penetration of a hypodermic needle is stopped without engaging the needle tip.
Figure 4B:
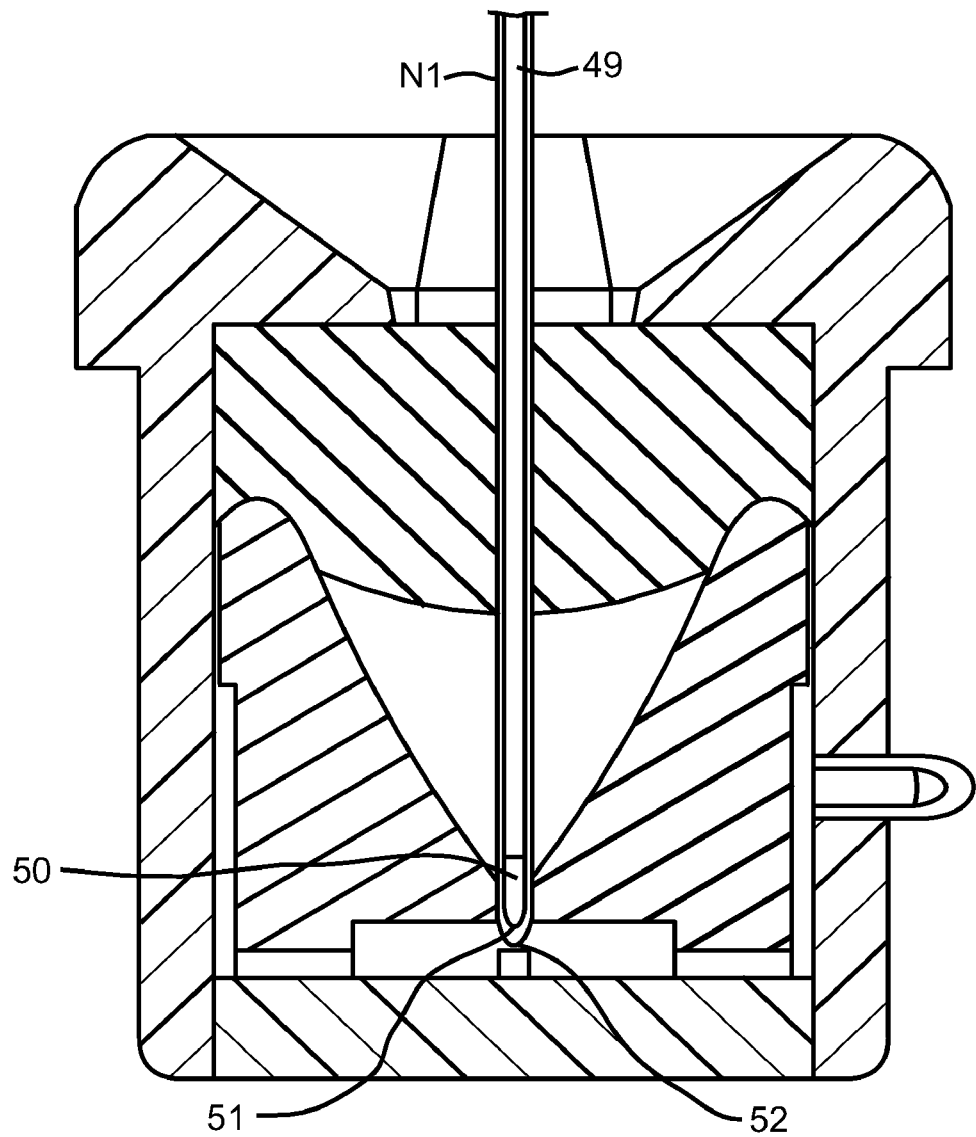
FIG. 4B is identical to FIG. 4A but shows the needle rotated by 90°.
Figure 5:
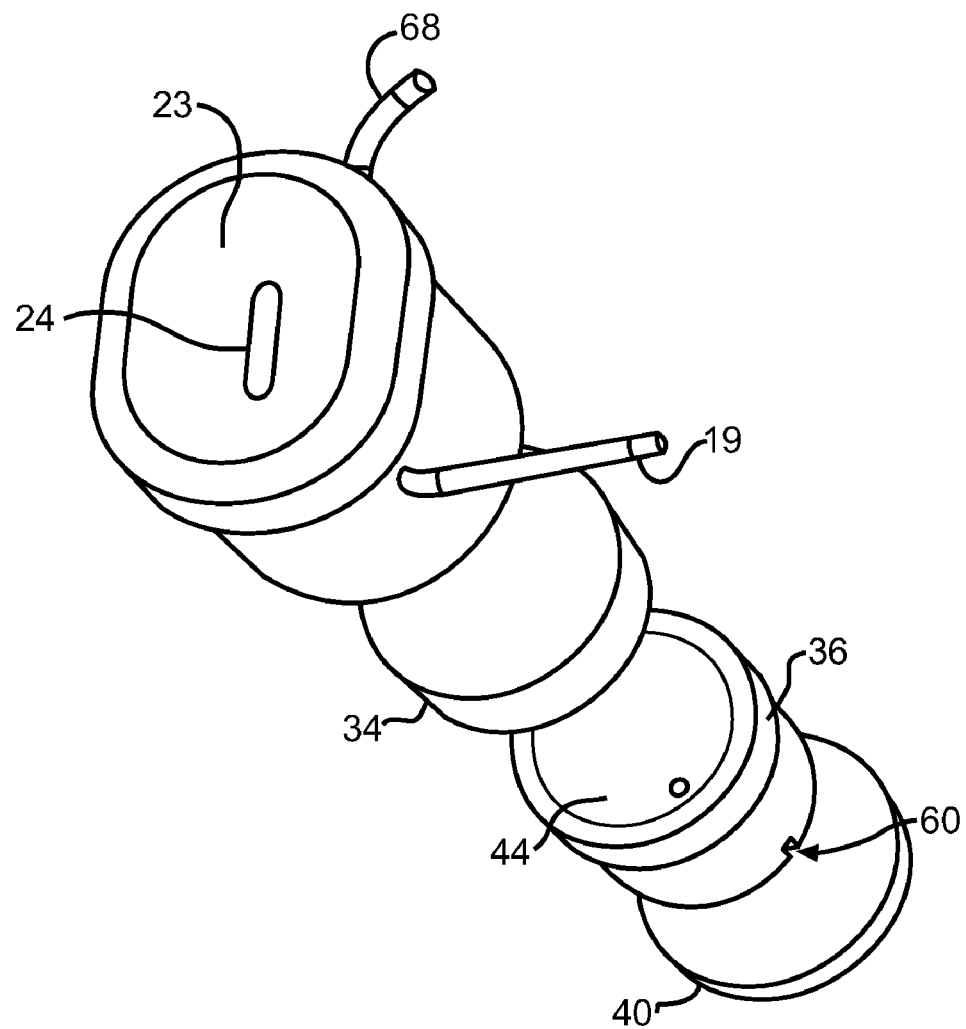
FIG. 5 is an exploded perspective view of the needle receiving port of FIG. 3.
Figure 6:
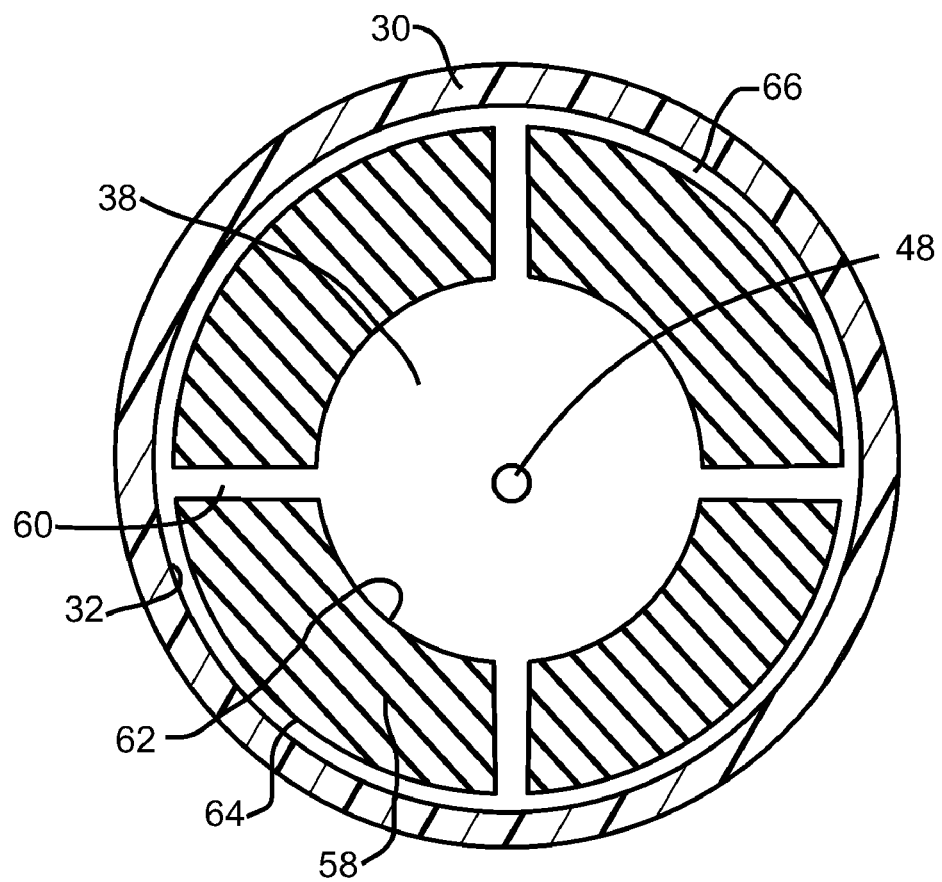
FIG. 6 is a sectional view taken substantially along the plane 6-6 of FIG. 2.

More particularly, FIGS. 4A and 4B depict an exemplary needle N1 having a cannula 49 and a point end 50 formed by an oblique surface 51. The point end terminates at a needle tip 52. As depicted in FIG. 4A, the outer diameter of the cannula 49 is represented by D1. The point end 50 has an outer diameter which diminishes from D1 adjacent to the cannula to D2 (close to zero) at the needle tip 52. The axial length of the point end 50 is represented by L1. In accordance with the present invention, the stop hole 48 diameter D3 is selected to be less than D1 and greater than D2. Furthermore the depth of stop hole 48 is selected such that L2, the sum of the hole's axial length plus an obstruction-free depth there beneath, is longer than the axial length L1 of the needle point end 50.

In use, the needle point end 50 will be inserted into the port to pierce the septum 34. The point end will then be guided by side wall 45 of recess 44 into stop hole 48. Because D1>D3>D2, the point end 50 will project into hole 48 with the oblique, or bevel, surface 51 engaging the stop member 36 adjacent to the hole 48. Because L2>L1, the needle tip 52 is held out of engagement with any surface thereby avoiding tip damage. In other words, the stop member 36 performs the function of preventing the pointed distal tip 52 of the needle from reaching the end of the unobstructed region by engaging the beveled surface 51.

In the preferred embodiment of the invention, the needle stop member 36 is relieved at 54 to form a particulate chamber 38 between the bottom cover 40 and the stop member 36. The hole 48 opens into the particulate chamber 38. The circumferential wall 58 (FIG. 6) of the particulate chamber 38 has one or more radial openings 60 dimensioned no larger in any direction than a dimension M. The opening(s) 60 extend radially outward from the inner surface 62 to the outer surface 64 of the circumferential wall 58 to a circumferential fluid passageway 66. An inlet tube 68 (FIG. 2) and an outlet tube 70 are coupled to the passageway 66. The inlet tube 68 typically carries fluid from the aforementioned reservoir and fluid transfer means (not shown) and the outlet tube typically carries fluid to the catheter port 18. By limiting the dimensions of openings 60, the chamber 38 will retain any particulate matter greater than the dimension M, which otherwise could be disadvantageously introduced by the needle into the fluid flow to the catheter.

From the foregoing, it should be recognized that an improved needle receiving port has been disclosed herein characterized by a stop member having a hole dimensioned to receive a needle point end for stopping axial penetration of the needle without engaging the needle tip. Moreover, the preferred embodiment efficiently incorporates a chamber for trapping oversized particles.

Although only a single specific embodiment has been described in detail herein, it should be understood that this embodiment is exemplary of various alternative configurations which may occur to those skilled in the art which are consistent with the teachings of the present invention and within the scope of the appended claims.

The invention claimed is:

1. An apparatus, comprising:
    a hypodermic needle having a cannula defining an outer diameter D1, a pointed end with a pointed distal tip defining an outer diameter D2 and a beveled surface extending from the pointed distal tip to the cannula and defining an axial length L1 with an outer diameter that diminishes from the cannula outer diameter D1 to the pointed distal tip outer diameter D2; and
    an implantable port including
        a port body,
        a septum associated with the port body, and
        a needle stop member associated with the port body including a stop hole with an inlet defining a diameter D3 that is less than the outer diameter D1 of the beveled surface and is greater than the diameter D2 of the pointed distal tip and an obstruction-free axial length L2 that is greater than the axial length L1 of the beveled surface, whereby said beveled surface will engage said needle stop member at said hole to stop axial penetration by said needle without engaging said pointed distal tip.

2. An apparatus as claimed in claim 1, further comprising:
    a particulate collection chamber formed in said needle stop member for accepting fluid from said hypodermic needle through said needle stop hole;
    at least one fluid outlet for discharging fluid from said chamber; and wherein
    said fluid outlet is dimensioned such that particulates larger than a predetermined size will be trapped in said chamber.

3. An apparatus as claimed in claim 2 further including:
    a cavity in said needle stop member formed by an interior side wall sloping into said stop hole inlet.

4. An apparatus as claimed in claim 3 wherein said septum overlays the said cavity.

5. An apparatus as claimed in claim 4 further including a needle entrance opening, overlaying said septum, dimensioned to only pass needles having an outer diameter equal to or smaller than the cannula outer diameter D1.

6. An apparatus as claimed in claim 1 further including:
    a cavity in said needle stop member formed by an interior side wall sloping into said stop hole inlet.

7. An apparatus as claimed in claim 6 wherein said septum overlays the said cavity.

8. An apparatus claimed in claim 7 further including a needle entrance opening, overlaying said septum, dimensioned to only pass needles having an outer diameter that is equal to or smaller than the cannula outer diameter D1.

9. An implantable infusion device for use with a hypodermic needle having a cannula defining an outer diameter, a pointed distal tip end defining an outer diameter, and a beveled surface defining an axial length with an outer diameter that diminishes from the cannula outer diameter to the pointed distal tip end outer diameter, the implantable infusion device comprising:
    a housing including a pump;
    a port, carried by the housing, including
        a needle entrance opening defining a length and a width,
        an unobstructed region defining an end, and
        means, located between the needle entrance opening and the end of the unobstructed region, for preventing the pointed distal tip end of the needle from reaching the end of the unobstructed region by engaging the beveled surface; and
        a septum between the needle entrance opening and the means for preventing.

10. An implantable infusion device as claimed in claim 9, wherein
    the width of the needle entrance opening is substantially equal to the cannula outer diameter; and
    the length of the needle entrance opening is greater than the width.

11. An implantable infusion device as claimed in claim 9, further comprising:
    a port outlet; and
    a filter located upstream from the port outlet and downstream from the means for preventing.

* * * * *